US006518261B2

(12) United States Patent
Slaga et al.

(10) Patent No.: US 6,518,261 B2
(45) Date of Patent: Feb. 11, 2003

(54) USE OF EUGENOL IN COMBINATION WITH OTHER CHEMOPREVENTATIVE AGENTS AS PROPHYLAXIS FOR CANCERS

(75) Inventors: Thomas J. Slaga, Austin, TX (US); Addanki P. Kumar, Denver, CO (US); William Alworth, New Orleans, LA (US)

(73) Assignee: Oncology Sciences Corporation, Austin, TX (US)

( * ) Notice: Subject to any disclaimer, the term of this patent is extended or adjusted under 35 U.S.C. 154(b) by 0 days.

(21) Appl. No.: 09/780,269

(22) Filed: Feb. 9, 2001

(65) Prior Publication Data

US 2002/0006918 A1 Jan. 17, 2002

Related U.S. Application Data

(63) Continuation-in-part of application No. 09/527,283, filed on Mar. 17, 2000, now abandoned, and a continuation-in-part of application No. 09/777,151, filed on Feb. 5, 2001.

(51) Int. Cl.[7] ........................ A61K 31/56; A61K 31/075

(52) U.S. Cl. ........................................ 514/171; 514/720
(58) Field of Search ................................. 514/171, 720

(56) References Cited

U.S. PATENT DOCUMENTS 5,958,892 A * 9/1999 Mukhopadhyay et al. .... 514/44
6,136,992 A * 10/2000 Ram et al. .................. 552/614

FOREIGN PATENT DOCUMENTS

WO 96/30012 * 10/1996
WO 99/22728 * 5/1999

OTHER PUBLICATIONS

Sukumaran et al., "Inhibition of tumor promotion in mice by eugenol". Indian J. Physiol. Pharmacol., vol. 38(4), pp. 306–308, 1994.*

* cited by examiner

Primary Examiner—Barbara P. Badio
(74) Attorney, Agent, or Firm—David G. Henry

(57) ABSTRACT

The use of eugenol, alone and in combination with 2-methoxyestradiol (2-ME) in the context of prostate cancer prophylaxes and treatment.

4 Claims, 2 Drawing Sheets

USE OF EUGENOL IN COMBINATION WITH OTHER CHEMOPREVENTATIVE AGENTS AS PROPHYLAXIS FOR CANCERS

CITATION TO PRIOR APPLICATION

This is a continuation-in-part with respect to U.S. application Ser. No. 09/527,283, filed Mar. 17, 2000, now abandoned, from which priority is claimed under 35 U.S.C. §120 and under provisions of the Patent Cooperation Treaty. This is also a continuation-in-part with respect to U.S. application Ser. No. 09/777,151, filed Feb. 5, 2001, which is also a continuation in part of U.S. application Ser. No. 09/527,283, filed Mar. 17, 2000.

BACKGROUND OF THE INVENTION

A. Field of the Invention

The present invention relates to the prevention and treatment of cancer through the use of chemopreventative agents.

B. Background of the Invention

Prostate cancer is the most common malignant transformation that occurs in men and its incidence is increasing at an alarming rate. Prostate cancer ranks as the most serious task facing both doctors and their male patients. Unfortunately, the major cause of death from prostate cancer comes in the hormone-refractory metastatic stage of the disease for which no treatment options are available at present.

Complicating the diagnosis and treatment of prostate cancer is the fact that prostate cancer remains latent and harmless in most individuals; clinically evident in many individuals, and virulent in still others. These variations in the expression of prostate concern make it even more difficult to derive efficacious treatment regimens. The therapies that are now available are associated with side effects which include impotence in about 59.9% men after 18-months of prostatectomy.

Over the past several years chemoprevention has been established as a meaningful approach to control malignancy. Chemopreventative approaches use either natural and/or synthetic compounds to intervene in the early pre-cancerous stages of carcinogenesis before cancer actually begins and thus having a greater chance of total cure. Like most cancers, prostate cancer is a complex process involving alterations in the balance between cell proliferation and cell death and accumulation of a series of genetic changes. Such an alteration exists in prostate cancer and in benign prostate hyperplasia (BPH). In BPH, the apoptotic index (percentage of cells undergoing apoptosis) is significantly reduced in the epithelial cells, basal cells and the stromal cells, while at the same time the proliferative index is significantly increased in all three cell types. These changes occur over a long period of time thus providing a large window of opportunity to i) prevent its induction; ii) inhibit the development of pre-invasive or invasive neoplasia and iii) its progression by using chemopreventative agents.

It is well known that prostate cancer is highly heterogeneous in that the tumor contains a population of both androgen-dependent and independent cells and also cells at different stages of transition between androgen-dependence and independence. Androgen ablation is, to date, the therapy of choice and is widely used to inhibit prostate cancer in the initial stages of prostate concern; however, the likelihood of recurrence of tumors (androgen-independent) limits this therapeutic approach. The average survival time after failing androgen-ablation therapy is about 12 months.

Prostate specific antigen (PSA) has traditionally been used as a tumor marker to detect prostate cancer. Many studies have demonstrated that most of the patients with established benign prostatic hyperplasia (BPH) undergoing prostatectomy have abnormal levels of PSA. 10 years after surgery approximately 25% of patients with PSA levels between 4–10 ng/ml; 70% between 10–20 ng/ml and 72% for men with PSA levels greater than 20 ng/ml develop prostate cancer. In addition, men with PSA levels of 2–4 have a 30% chance of developing prostate cancer after 5 years.

SUMMARY OF THE INVENTION

In view of the above, there is a dire need for more effective preventative and therapeutic approaches in dealing with prostate cancer specifically and, of course, all cancers for which there is no presently available and reliable cure.

It is, therefore, an object of the present invention to provide a new modality for the prevention of cancer.

It is another object of the present invention to provide a new modality for the treatment of cancer.

It is another object of the present invention to provide a new modality for the treatment of prostate cancer.

It is another object of the present invention to provide a method by which the known substance of eugenol may be employed in a new and unobvious manner in the prevention and/or treatment of cancers, including prostate cancer.

It is another object of the present invention to provide a method by which the known substance of eugenol may, in combination with synergistic compounds, including 2-ME, be employed in the prevention and/or treatment of cancers, including prostate cancer.

In satisfaction of these and related objects, disclosed and claimed herein is the use of eugenol, alone and in combination with 2-methoxyestradiol (2-ME) in the context of prostate cancer prophylaxes and treatment.

Eugenol is a major component of the essential oils from bay leaves and the buds of cloves (Eugenia Caryophyllata). It is widely used as a flavoring agent in food products, pharmaceuticals products and also as an analgesic in dentistry. However, nothing has been heretofore known about eugenol's capacity for preventing and treating cancer.

The use of eugenol either alone or in combination with 2-ME offers the following important advantages: i) since eugenol has been used as an analgesic successfully in the dentistry, toxicity is unlikely; (ii) cell cycle analysis data indicated that eugenol inhibited the growth of suspect cells without any significant alterations in the cells cycle profile, thereby indicating a different mechanism of action than that of 2-ME when used in the same context; (iii) yet, eugenol demonstrated synergistic activity with 2-ME. The present inventors have shown that 2-ME inhibits the growth of cells by inducing apoptosis and blocking cells in G2/M phase. Therefore induction of cell death pathway by 2-ME and growth inhibition by eugenol through a different pathway presents a tremendous new weapon for use in preventing and combating cancer.

DETAILED DESCRIPTION OF THE PREFERRED EMBODIMENT

The present inventors have used androgen-dependent (LNCaP) and androgen-independent (DU145) human prostate cancer cell lines to investigate the effect of eugenol and isoeugenol on cancer treatment. These cells were treated with different concentrations of eugenol (0.5, 1, 3, 5 and 10 mM). Cell growth was monitored every 24 hours by counting the increase in the cell number using trypan blue exclusion assay. These results were also confirmed by using cell proliferation assay kit.

Figure 1:
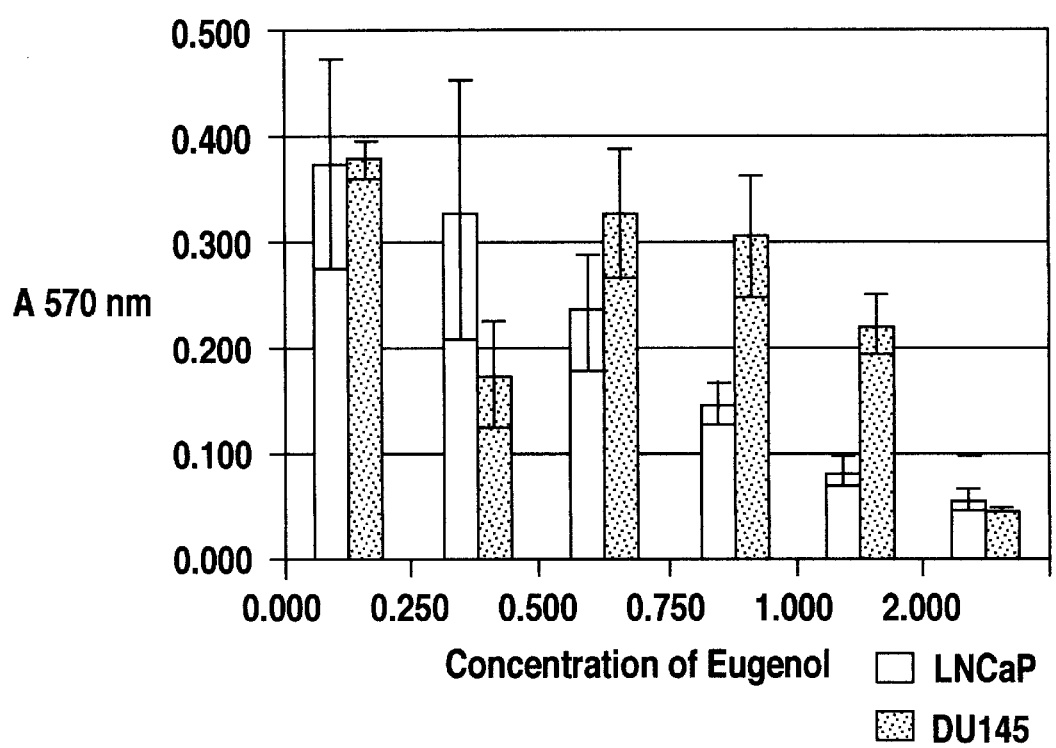
FIG. 1 is a graphical depiction of data establishing that eugenol inhibits the growth of LNCaP cells significantly—a concentration of approximately 0.75 mM being necessary to see 50% inhibition of growth of LNCaP cells—whereas a concentration of more than 2 mM was necessary to see similar effect in DU145 cells.

As shown in FIG. 1, eugenol inhibited the growth of LNCaP cells significantly. A concentration of approximately 0.75 mM was necessary to see 50% inhibition of growth of LNCaP cells whereas a concentration of more than 2 mM was necessary to see similar effect in DU145 cells.

Figure 2:
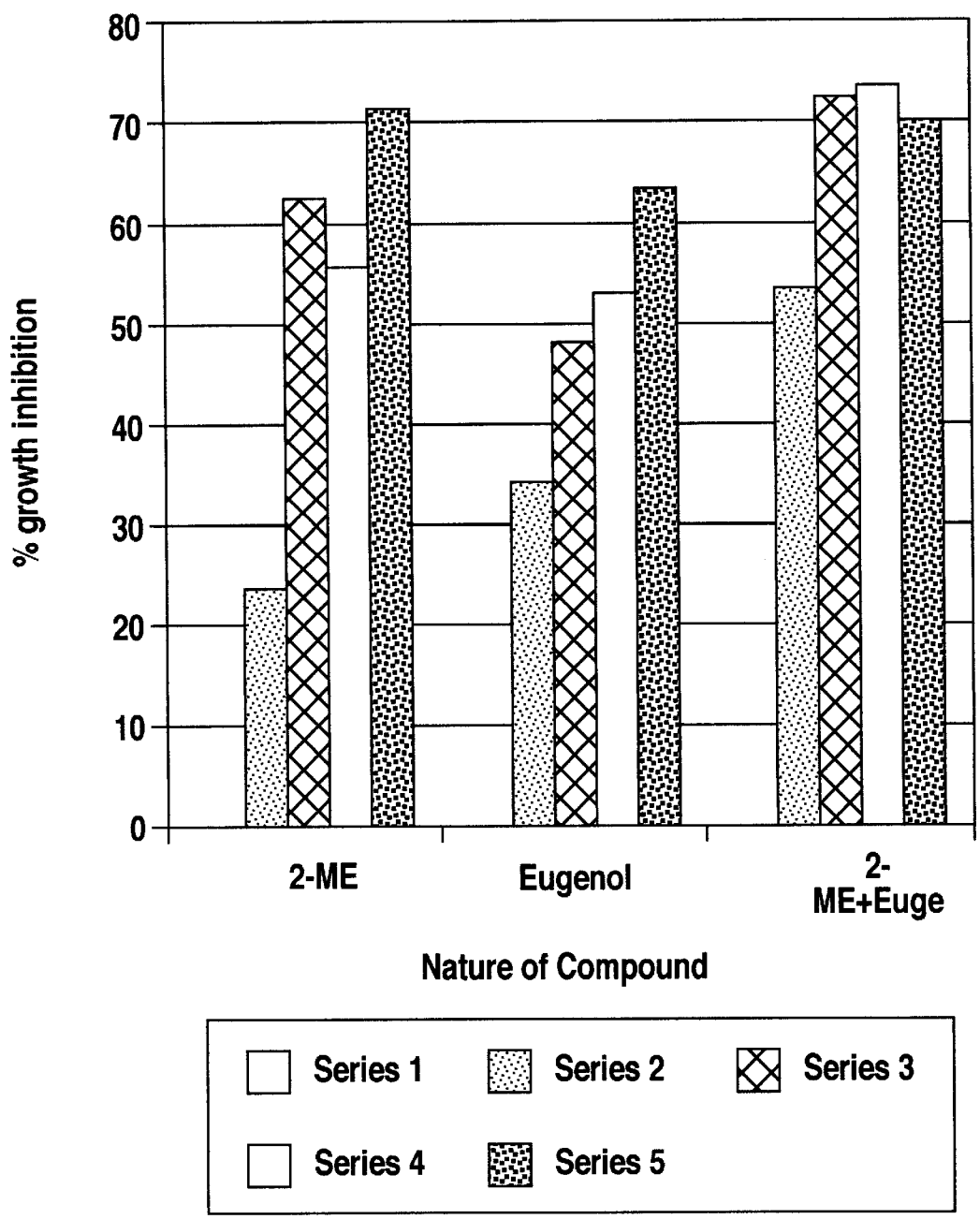
FIG. 2 is a graphical depiction of the percent growth inhibition of multiple cell line series, comparing 2-ME alone, eugenol alone and 2ME-combined with eugenol.

The investigational work of the present inventors also establish that eugenol works in combination with 2-ME to achieve even more impressive results. Cells were treated with either eugenol (0.25, 0.5, 0.75 or 1 mM) or 2-ME (0.5, 1, 2 or 3 mM) or both (0.25, 0.5, 0.75 or 1 mM of eugenol along with 0.5 mM of 2-ME). Cell growth was measured following 72 hours of treatment as described above. As shown in FIG. 2, 0.5 mM of 2-ME inhibited growth of LNCaP cells by about 20% and 0.25 mM of eugenol inhibited the growth by about 30%. However, combining both the agents showed more than 50% inhibition thereby establishing a synergistic activity of eugenol and 2-ME in combating cancer cells.

The mechanisms of action at work against the cell lines investigated thus far are reasonably expected to be equally efficacious in treating other cancers and pre-cancerous conditions, such BPH and the cancers of brain, liver, lung, colon and skin. Since both hormone-responsive and hormone-refractory prostate cancer cells are inhibited by eugenol, patients can be treated with eugenol after surgery to prevent the recurrence of hormone-refractory cancer. As indicated, the synergistic effects of eugenol and 2-ME provide an even more potent weapon against cancers.

Application to existing, in vivo tumors may be of varying means, including, but not limited to, direct injection, electrophoresis, and non-electromotive transdermal migration. Practitioners skilled in the use of chemopreventative agents will adjust dosages to meet the apparent needs of any particular patient, and the disclosure contained herein shall provide an enabling disclosure for the use of eugenol alone, and with the synergistic compound of 2-ME in the treatment or prevention of cancerous tumors.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A method for inhibiting the growth of cancerous and precancerous cell populations comprising the step of applying a therapeutic amount of eugenol and 2ME in combination to a cancerous or pre-cancerous prostate cell population for a sufficient time to observe arrest of growth of said population.

2. A therapeutic agent useful in the prevention and treatment of prostate cancerous tumors comprising therapeutic dossages of eugenol and 2-methoxyestradiol in combination.

3. A method of inducing apoptosis in cancerous tissues comprising the steps of:
    administering a therapeutic dosage of a composition containing 2-methoxyestradiol and eugenol in combination to a cancerous or pre-cancerous prostate tissues, said administration continuing at least until the initiation of cell apoptosis in said cancerous tissues.

4. A method for arresting growth of cancer tissues comprising the steps of:
    administering a therapeutic dosage of a composition containing 2-methoxyestradiol and eugenol in combination to a cancerous or pre-cancerous prostate tissue, said administration occurring at a time wbich, at least for some cells in said cancerous tissue, precedes cell division in the G2/M phase.

* * * * *